US009782777B2

(12) United States Patent
Mortillaro et al.

(10) Patent No.: US 9,782,777 B2
(45) Date of Patent: Oct. 10, 2017

(54) SAMPLE PLATE ASSEMBLY AND METHOD OF PROCESSING BIOLOGICAL SAMPLES

(75) Inventors: Michael J. Mortillaro, Webster, NY (US); Bruce R. Turner, Exeter, NH (US); David A. Cohen, Dedham, MA (US)

(73) Assignee: Thermo Fisher Scientific Oy, Vantaa (FI)

( * ) Notice: Subject to any disclaimer, the term of this patent is extended or adjusted under 35 U.S.C. 154(b) by 649 days.

(21) Appl. No.: 12/065,871

(22) PCT Filed: Sep. 5, 2006

(86) PCT No.: PCT/FI2006/050379
§ 371 (c)(1),
(2), (4) Date: May 12, 2008

(87) PCT Pub. No.: WO2007/028861
PCT Pub. Date: Mar. 15, 2007

(65) Prior Publication Data
US 2008/0220481 A1  Sep. 11, 2008

Related U.S. Application Data

(60) Provisional application No. 60/714,816, filed on Sep. 6, 2005.

(30) Foreign Application Priority Data

Sep. 6, 2005  (FI) .................................... 20050882

(51) Int. Cl.
*B01L 3/00* (2006.01)
*G01N 35/02* (2006.01)

(52) U.S. Cl.
CPC ... *B01L 3/50855* (2013.01); *B01L 2300/0829* (2013.01); *G01N 35/028* (2013.01)

(58) Field of Classification Search
CPC ......... B01L 2300/0829; B01L 3/50855; G01N 35/028
See application file for complete search history.

(56) References Cited

U.S. PATENT DOCUMENTS

| | | |
|---|---|---|
| 3,713,985 A | 1/1973 | Astle |
| 3,992,265 A | 11/1976 | Hansen |
| D269,702 S | 7/1983 | Suovaniemi et al. |
| 4,659,222 A | 4/1987 | Ekholm |
| 4,682,891 A * | 7/1987 | de Macario et al. ......... 356/244 |
| 4,948,564 A * | 8/1990 | Root et al. .................... 422/101 |
| 5,084,246 A * | 1/1992 | Lyman et al. ................ 422/101 |
| RE34,841 E | 1/1995 | Suovaniemi et al. |
| 5,650,125 A * | 7/1997 | Bosanquet ............ B01L 3/5021 422/548 |
| 5,922,266 A | 7/1999 | Grove |
| 5,968,439 A | 10/1999 | Grove |
| 6,051,191 A | 4/2000 | Ireland |
| 6,118,582 A | 9/2000 | Del Buono |
| 6,340,589 B1 | 1/2002 | Turner et al. |
| 6,669,911 B1 | 12/2003 | Swanson |
| 2002/0022263 A1 | 2/2002 | Monahan et al. |
| 2002/0151045 A1 | 10/2002 | Turner et al. |
| 2003/0087271 A1 * | 5/2003 | Ebersole et al. .................. 435/6 |
| 2003/0215940 A1 | 11/2003 | Lacey et al. |
| 2004/0005640 A1 * | 1/2004 | Mizejewski .................... 435/7.9 |
| 2004/0182770 A1 * | 9/2004 | Clark et al. ................. 210/321.6 |
| 2004/0200580 A1 | 10/2004 | Guthrie et al. |
| 2005/0058578 A1 | 3/2005 | Guelzow et al. |
| 2005/0135974 A1 | 6/2005 | Harvey et al. |
| 2005/0265901 A1 * | 12/2005 | Sinclair et al. ............... 422/104 |

FOREIGN PATENT DOCUMENTS

| | | |
|---|---|---|
| EP | 39145 A1 | 11/1981 |
| EP | 0408280 A2 | 1/1991 |
| EP | 415307 A2 | 3/1991 |
| EP | 1316360 A2 | 6/2003 |
| EP | 1457553 A1 * | 9/2004 |
| EP | 1457553 A1 | 9/2004 |
| GB | 2374815 A | 10/2002 |
| GB | 2396317 A | 6/2004 |

(Continued)

OTHER PUBLICATIONS

Society for Biomlecular Screening, SBS Recommended Microplate Specifications, May 1999, pp. 1-4.*
Frank, The SPOT-synthesis technique Synthetic peptide arrays on membrane supports—principles and applications, Journal of Immunological Methods 267 (2002) 13-26.*
Nunc* Immuno LockWell Strip Plates. <http://www.thermoscientific.com/wps/portal/ts/products/detail?navigationId=L10569&categoryId=81999&productId=12710664> Accessed on Aug. 9, 2010.
Machine generated English translation of Abstract for DE-2435317.
Office Action issued in U.S. Appl. No. 11/623,025 dated Jun. 24, 2010.

(Continued)

*Primary Examiner* — Cynthia B Wilder

(57) ABSTRACT

The invention concerns a v-bottomed sample plate, a frame for sample plates and a kit and method for processing biological samples. The kit comprises a tray assembly and a plurality of sample plates designed to fit into the tray assembly. The tray assembly comprises a frame having a central plate receiving portion having a width and length, whereby said tray assembly is capable of accommodating the sample plates side by side in the plate receiving portion. Each of the sample plates contains a plurality of individual sample wells arranged in a grid, the dimension of the plate in a first direction being at maximum the width of the frame and the dimension of the plate in a second direction being at maximum half of the length of the plate receiving portion of the of the frame, and means for enabling automated handling of the plates. The invention enables more efficient biomedical processing of samples.

13 Claims, 7 Drawing Sheets

(56) References Cited

FOREIGN PATENT DOCUMENTS

| WO | WO-8402775 A1 | 7/1984 |
| WO | WO-99/61152 | 12/1999 |
| WO | WO 9961152 A1 * | 12/1999 |
| WO | WO-01/07160 A2 | 2/2001 |
| WO | WO-01/52988 A1 | 7/2001 |

OTHER PUBLICATIONS

Office Action issued in U.S. Appl. No. 11/623,025 dated Mar. 23, 2010.
Office Action issued on Jun. 21, 2011 in corresponding Japanese Application No. 2008-529653.
Espacenet, English Machine Translation of WO0152988A1, published Jul. 26, 2001, retrieved from http://worldwide.espacenet.com on Nov. 9, 2015 (12 pages).

* cited by examiner

SAMPLE PLATE ASSEMBLY AND METHOD OF PROCESSING BIOLOGICAL SAMPLES

This application is the National Phase Under 35 U.S.C. §371 of PCT International Application No. PCT/FI2006/050379 which has an International filing date of Sep. 5, 2006, which claims priority to Finish Application No. 20050882 filed on Sep. 6, 2005, and also on U.S. Provisional Application No. 60/714,816 filed on Sep. 6, 2005, the entire contents of all applications listed above are hereby incorporated by reference.

BACKGROUND OF THE INVENTION

Field of the Invention

The present invention relates to devices for processing biological samples. In particular, the invention concerns a microtiter plate assembly comprising microtiter plates having a plurality of sample wells. Such plates are used, for example, in thermal cyclers for performing a Polymerase Chain Reaction (abbreviated "PCR") process. The present invention also concerns a method of processing biological samples.

Description of Related Art

Biological samples are processed in industrial and clinical diagnostics, pharmaceutical and research applications, and as processes have improved, the need for increasing the number and speed of samples processed has also increased. This has led to a standardization of sample containers based on a few, historically significant standards that have allowed users to utilize a large number of instruments or robotic handlers which were designed to operate within that standard.

The standards that are most commonly used are based on the formats of the microfuge tube, the microscope slide and the microtiter plate. Microfuge tubes come in several, usually non-interchangeable, sizes based on the desired size of the sample to be processed, and are usually used for liquid samples volumes of more than 0.01 ml to 1.5 ml. Microscope slides are utilized for tissue samples and very high density arrays of tiny samples that can be bound to the surface of the slide. Microtiter plates are built like arrays of very small microfuge tubes, and are available in a multitude of formats with varying materials, well geometries and sample densities, but all share the same basic footprint and are typically used for liquid samples that are between 10 µl and 500 µl in volume. It is interesting to note that several new technologies that have seen intensive development efforts in recent years, including microarrays and microfluidics applications, are almost always implemented to conform to one of these three standards in order to take advantage of the many tools developed for these standards.

Whilst the microfuge tube offers relatively high volume of reaction and low throughput of biological samples, the trend for clinical diagnostics, industrial microbial detection, and pharmaceutical and academic research has been able to reduce the volume of reaction and increase the throughput of these processes. To this end, high density microtiter plates and slide-based microarrays have become more commonly used. These formats are of particular interest because they offer the ability to perform parallel experiments, reduce reagent consumption, and confer the potential to utilize smaller, relatively less expensive laboratory and analytical instrumentation.

Microtiter plates are approximately 85 mm wide by 127 mm long by as many as 25 mm high. They come in several formats, but for molecular biology applications, 96-well and 384-well formats are, by far, the most common. 96-well microtiter plates typically consist of an 8×12 array of conical-shaped wells of 9 mm center-to-center pitch and an inner diameter of 5 to 6 mm. Depending on the variety of plate, each well can hold a maximum of 100 µl to 200 µl of reaction volume. 384-well plates halve the spacing, such that the plates now offer a 16×32 format, with 4.5 mm pitch, 3 to 3.5 mm inner diameters, and maximum sample volumes of 40 µl to 50 µl. Most biological chemistries performed in a microtiter plate are solution-based, but surfaced based chemistries can also be performed.

Microslide-sized arrays come in a variety of sample densities, but have the following general aspects in common: i) footprint of microarray typically is 25 mm by 75 mm, ii) generally based upon surface chemistries, and iii) typically do not have an individual three-dimensional aspect for addressing each sample. Sample densities can vary from a few thousand to over a hundred thousand per slide.

Microtiter plates and microarrays differ in their ability to address individual samples. Microtiter plates offer the well-to-well spacing and 3-dimensional aspect of a sample vessel, so that each well can be manipulated individually allowing for variation of both sample and reactants across a single plate. On the other hand, microscope-sized microarrays, for the most part, do not allow for every permutation of sample and reactants to be performed on a single microarray slide. The reason for this key difference is that the spacing on microtiter plates allows for standard pipetors and liquid handling robotic stations to both add and remove liquid from each well—thus allowing for unique combinations of sample and reactants to be applied across a single plate. Microarrays, however, tend neither to have the 3-D aspect to sample containment, nor the ability to be addressed by standard pipetors and liquid handling robots, which are generally required for such individualized reaction manipulation. It should be noted that there are a handful of microscope slide-based vessels that contain thousands to hundreds of thousands of pits or holes that confer a three-dimensional space in which to perform liquid-phase reactions. However, because the volumes of such spaces are measured in the picoliter range, and the density is so great, individual sample manipulation is impossible with commercially available liquid handler devices.

Thermal cyclers are instruments commonly used in molecular biology for applications such as PCR and cycle sequencing, and a wide range of instruments are commercially available. A subset of these instruments, which include built-in capabilities for optical detection of the amplification of DNA, are referred to as "real-time" instruments. Although these can sometimes be used for different applications than non-real-time thermal cyclers, they operate under the same thermal and sample preparation parameters.

The important parameters that govern how well a thermal cycler operates are: uniformity, accuracy and repeatability of thermal control for all the samples processed, ability to operate in the environment of choice, speed of operation, and sample throughput. As the processes get more complicated and the amount of automation increases, the importance of compatibility with and flexibility between different process phases and technologies is emphasized.

Sample throughput needs have come about over time. All currently produced thermal cyclers can be divided up into groupings based on how they accommodate samples. The first instruments were built to accommodate a small number of tubes which were individually processed and loaded into the cycler (example: Perkin-Elmer 4800). As sample throughput needs grew, instruments were developed to accommodate plastic trays (microtiter plates) that were essentially arrays of 96 or 384 tubes (examples: Perkin-Elmer 9600, MJ Research PTC-200, Eppendorf MASTER-CYCLER®). Both of these formats tend to utilize metal blocks to heat and cool the tubes, which places some limits on the speed of thermal cycling due to the time needed to heat and cool the mass of the metal block.

The vast majority of thermal cyclers in use today are block based thermal cyclers that accommodate microtiter plates. The reason for this, despite the potential for slow cycling speeds of these instruments, is that microtiter plates can be used with a wide range of liquid volumes, and the actual sample throughput is tends to be quite high in terms of total number of samples that can be processed in a given timeframe. This last aspect is only partially a function of the instrument itself; it is also dependent upon the equipment that is available to process and load the samples both before and after the thermal cycling reaction. The vast majority of microtiter plates in use conform to a set of standards codified by the Society for Biomolecular Screening (SBS) over the last decade. The plates typically have 6, 24, 96, 384 or even 1536 sample wells arranged in a 2:3 rectangular matrix. The standard also governs well dimensions (e.g. diameter, spacing and depth) as well as plate properties (e.g. dimensions and rigidity).

A number of robots designed to specifically handle SBS microplates have been developed. These robots may be liquid handlers which aspirate or dispense liquid samples from and to these plates, or "plate movers" which transport them between instruments. Also plate readers have been developed, which can detect specific biological, chemical or physical events in samples being processed in the plates.

Adherence to the SBS Microtiter Plate Standards has allowed the easy integration of robotics solutions such as liquid handling machines into the sample preparation process which has had a profound impact on the ability to increase sample throughput. It can therefore be concluded that innovations that will further increase sample throughput must do so without compromising the ability to work within the SBS specifications.

EP-publication 408280 discloses a specially designed multiwell plate format for processing of samples manually in parallel fashion. Publications related to parallel processing of microscope slides and similar plates include WO 99/61152, DE 10002666, US 2004/071605 and US 2005/135974.

SUMMARY OF THE INVENTION

It is an aim of the present invention to provide a novel microtiter plate assembly, which improves processability of sample patches.

It is another aim to provide a novel sample plate.

In particular, it is an aim of the invention to provide a microtiter plate system which moves a step further in the evolution of biomedical processing formats by allowing the advantages of small size, reduced reagent volume, and parallel nature of the microscope format to be combined with the commonly used types of liquid manipulation and instrument compatibility of the microtiter plate format.

It is still a further aim of the invention to provide a novel method of processing biomedical samples using said microtiter plate system.

These and other objects, together with the advantages thereof over known methods and apparatuses, are achieved by the present invention, as hereinafter described and claimed.

The invention is based on the idea of incorporating individually addressable wells which have a significant three-dimensional sample volume into a plate having the footprint of a microscope slide. A plurality of these microscope-sized plates can be combined, side by side, into a novel tray assembly to form a larger plate unit, in particular, a plate unit having the dimensions of a standard microtiter plate as set forth by the SBS.

The sample processing kit according to the present invention thus comprises a frame and a plurality of microtiter plates designed to fit into the frame to form a tray assembly. The frame has a generally rectangular shape and comprises a set of two parallel, generally elongated first frame elements and two parallel generally elongated second elements. The central axes of the first elements are generally perpendicularly arranged with respect to the central axes of the second elements, and the first and second elements are perpendicularly connected to each other to form the rectangular frame which defines a central sample plate receiving portion, which can be in the form of a central recess, in particular a central opening. This opening may be devoid of any secondary structural elements, or may be comprised of a series supporting elements in which one or more wells may fit within. The frame is designed to hold a plurality of sample plates, which can be mounted or assembled side by side into the frame such that they are supported by the frame receiving portion of the frame. Each of the sample plates comprises a plurality of individual sample wells arranged in a grid. Generally, the sample plates are of a v-bottom—type, meaning that they comprise a plurality of individual wells formed of thin wall material, whereby sample wells are adapted to at least partially protrude through the plate-receiving portion of the frame.

The dimension of the plates in a first direction is at maximum the dimension of the frame in the corresponding direction and the dimension of the plate in a second direction perpendicular to the first direction is at maximum a half of the dimension of the central recess or opening of the frame in that direction. Each of the plates comprise means for enabling addition of the plates to and removal of the plates from the frame in an automated fashion by a robotic system.

The sample plate according to the invention comprises a plurality of wells arranged in a grid having a predetermined pitch. The number of wells in a first dimension of the plate corresponds to the number of wells in a first dimension of an SBS standard microtiter plate and the number of wells in a second dimension of the plate corresponds to a fraction of the number of wells in a second dimension of the SBS standard microtiter plate.

The method of processing biological samples according to the invention comprises, in any order, the steps of:
  providing a plurality of sample plates, each of the plates comprising a plurality of sample wells arranged in a grid;
  loading the sample plates with biological samples;
  providing a tray for holding a plurality of sample plates; and
  placing the sample plates side by side in the tray for enabling simultaneous processing of the samples.

More specifically, the sample plate kit according to the present invention is mainly characterized by a tray assembly and a plurality of sample plates wherein the sample plates are microtiter plates suitable for thermal cycling according to the PCR process, thus being of a v-bottom-type, whereby the sample wells are adapted to at least partially protrude through the plate-receiving portion of the frame.

The sample plate is mainly characterized by what is stated in the characterizing in that the sample plate is a microtiter plates suitable for thermal cycling according to the PCR process, thus being of a v-bottom-type.

The method according to the present invention for processing of biological samples is characterized by the steps of:
- providing a plurality of v-bottomed microtiter sample plates suitable for thermal cycling according to the PCR process, each of the plates comprising a plurality of sample wells arranged in a grid,
- loading the sample plates with biological samples, and
- providing a tray assembly comprising a frame having two parallel first frame elements and two parallel second frame elements, the frame elements being perpendicularly connected to each other to form a generally rectangularly shaped frame, the inner edges of the frame elements defining a central opening and the frame being capable of accommodating and immobilizing a plurality of adjacent sample plates such that their sample wells at least partially protrude through the central opening of the frame, and
- placing the sample plates side by side in the tray assembly in an automated fashion by a robotic system for enabling simultaneous processing of the samples in a thermal cycling instrument, and
- processing the samples according to the PCR process in said thermal cycling instrument.

Considerable advantages are obtained by means of the invention. Thus, the sample tray allows for low volume and high density of biological samples to be processed in a wide variety of laboratory instruments. The individual sample plates can be addressed and processed separately either before of after their joint processing without having to move samples between wells. As the plates can be manufactured standard-sized in the first direction, and the frame can be manufactured to fully conform to the standards, use of the system does not necessitate considerable equipment updates. Thus, the invention brings the benefits of automated parallel processing to the field of v-bottom microtiter plate technology.

In particular, the present format, in regards to performing molecular biological reactions, allows for the potential of:
1. higher sample density (2.25 mm pitch and less),
2. lower reagent usage,
3. individually addressable samples, and
4. creation of smaller, less expensive instrumentation to perform biological assays, than are afforded by SBS standard microtiter plates.

Higher sample densities can be achieved because a smaller sized plate is physically more stable (especially to thermal stresses that can cause warping and shrinkage), requiring thinner structural walls and less material. The thinner walls and fewer structural details required, allow for smaller wells, packed more tightly together.

Lower reagent usage is a result of the smaller wells. Smaller wells have less surface area (and head space) to lose samples via vapor pressure, and the smaller conical bottoms make sample retrieval repeatable.

Typically, higher density formats used for molecular biological reactions either do not allow individual reactions to be manipulated, or if individual manipulation is allowed, then having the ability to manually adjust reactants for each reaction is limited. As discussed above, the slide-sized plate format will allow for a dense array of individual reaction chambers, moreover these chambers (or wells) will be of sufficient size (3-dimensional space) and pitch to allow liquid to be dispensed and removed, limited only by the liquid dispensers capabilities.

Building smaller, less expensive instrumentation is also a function of the smaller size of the plate. An example might be a thermal cycler designed for the smaller, slide-sized plate format. Such an instrument would have lower power consumption because only ¼ of the standard microtiter plate area needs to be heated and cooled. Also related, the heat sink for the thermally conductive sample holder could also be up to ¼ the size because of the plate format and lower power usage. Both a smaller power supply and smaller heat sink could translate to a significantly smaller system, as the power supply and heat sink may contribute as much as 50% of the instrument volume requirements.

Furthermore, the ability for several, typically four, of these reduced-sized plates to be combined into one microtiter-sized tray assembly still maintains some of the key advantages of microtiter-sized plates such as use of standard liquid handling devices and compatibility with existing laboratory and analytical instrumentation, such as thermal cyclers.

According to an aspect of the invention, the sample plates according to the embodiments of the invention can be used both in combination with the novel tray disclosed in this document, but also separately. As the plates conform to the SBS standards in one dimension, they are highly compatible with existing plate-handling devices which typically handle the plates in a one-dimensional manner. When needed, several such plates can be mounted on a tray assembly to enable their joint processing, for example, in a conventional SBS-compliant thermal cycler. That is, the sample plates enable a more flexible process, where several sample groups can be addressed both separately and together. In prior art plates, such an operation would require re-dispensing of the samples.

Moreover, the sample plates can be used in smaller and/or faster, probably portable, thermal cyclers that, have the potential to become commonly used in the research and diagnostic communities.

Most semi-automated and fully automated liquid handlers for molecular biological reactions remove and dispense liquid as either a single tip, a row of 4, 8, or 12 tips, or an array of 96 or 384 tips (in a 8×12 or 16×24 tip array respectively). Such liquid manipulating instruments are designed to hold a standard, SBS-compatible, microtiter plate in a position relative to the dispensing tips and either move the tips, or the plate (or both) to address the appropriate wells. The key to maintaining the compatibility is to offer a tray having the correct X-Y dimensions, and inter-compatible plates having the correct well-to-well spacing. Like with liquid handling devices, common types of laboratory equipment and analytical instrumentation have been designed to work specifically with microtiter plates of particular X-Y dimensions and well-to-well spacing. The combined reduced-sized plate and frame assembly maintains both of these standards, thus allow simple compatibility with these machines.

In the case of the small sample plate that is ¼ the size of a microtiter plate (corresponding to a slide-sized plate), a special benefit is realized as standard laboratory equipment designed to handle microscope slides can also be utilized for handling of this small sample plate.

Next, the invention will be described more closely with reference to the attached drawings, which represent an exemplary embodiment of the invention.

BRIEF DESCRIPTION OF THE DRAWINGS

FIG. 2b depicts a detailed side view of the tray of FIG. 2a;

FIG. 2c depicts a detailed side view of the tray of FIG. 2a;

FIG. 3 illustrates a cross-sectional view of the tray detail A-A shown in FIG. 2a;

FIG. 4b depicts a side view of the plate of FIG. 2a;

FIG. 4c depicts a side view of the plate of FIG. 2a;

FIG. 5a shows a cross-sectional view of the plate detail A-A shown in FIG. 4a.

DETAILED DESCRIPTION OF THE INVENTION

Figure 1A:
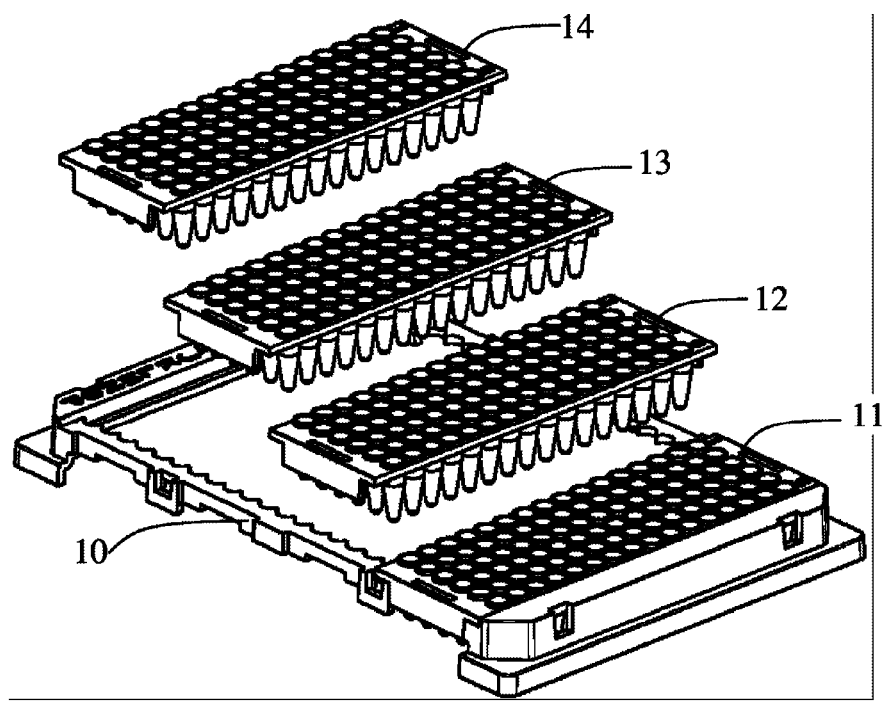
FIG. 1a shows a perspective view of a tray and slide-sized plate kit according to a preferred embodiment of the invention.

As described previously, generally, the sample plate assembly according to the invention comprises a frame having two parallel first end portions and two parallel second end portions. The end portions, i.e. frame elements, are connected to each other from their ends to form an essentially rectangular mounting structure for microtiter plates. Thus, the inner edges of the end portions define a central opening, into which the wells of the sample plates can be fitted such that the end portions of the frame immobilize the plates relative to the frame. Also, as mentioned in the previous section, the central opening may or may not contain a secondary support grid. The outer peripheral dimensions of the frame meet the SBS standards, whereby the present sample plate assembly can be used for processing of biological samples in, e.g., thermal cyclers, which are conventionally operating on SBS standard microtiter plates.

It should be pointed out that the following description of the invention mainly focuses on two preferred embodiments of this invention: a 96-well slide-sized plate and a 384-well slide-sized plate. The ratio of the number of wells in each direction in these embodiments is 3:8. However, the tray assembly can be such that different kinds of plates fit into it or it can be designed individually for each plate type.

It should also be noted that, in the following, the terms "sample plate assembly" and "sample plate kit" will be interchangeably used for designating an assembly comprising a frame structure having an inner opening and a plurality, of individual sample plates, which can be fitted into the frame.

Although the preferred embodiment of the invention comprises a structure, in which the frame elements form an open frame, in which the wells of the microtiter plate extend through the central opening defined by frame elements, in order to allow for unrestricted contact with for example the holder/heat transfer means of a thermal cycler, it is also possible to construct the frame with a backing sheet or plate, preferably provided with openings for allowing for unrestricted heat transfer. Such a backing plate will reinforce the structure. Therefore, even if the following description identifies the portion of the tray capable of receiving the sample plates as an "opening", it should be understood that embodiments wherein there is a recess or a plurality of recesses formed in a partly open frame structure are also included within the scope of the present invention.

The term "SBS standard plate" used herein is synonymous with the term "SBS conforming microtiter plate" and it denotes plates which conform with the set of standards codified by the Society for Biomolecular Screening (SBS) for microtiter plates. Generally, such plates have 6, 24, 96, 384 or even 1536 sample wells arranged in a rectangular matrix. Further, the SBS standard governs the dimensions (e.g. diameter, spacing and depth) of the wells and also the properties of the plates. (e.g. dimensions and rigidity). The second dimension of the sample plates used in conjunction with the present trays can be a submultiple of the corresponding dimension of a SBS microtiter plate standard, for example, ½, ⅓$^{rd}$, ¼$^{th}$ or ⅙$^{th}$ the size of such a plate, and they can constructed such that they conforms with the SBS standard 9 mm, 4.5 mm or 2.25 mm well pitch.

Figure 1B:
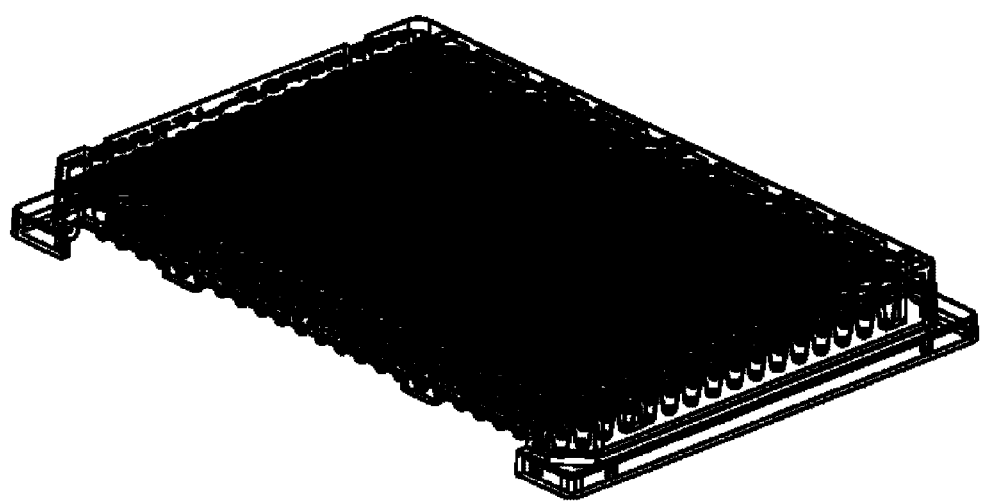
FIG. 1b shows a perspective view of a tray loaded with plates.
Figure 2A:
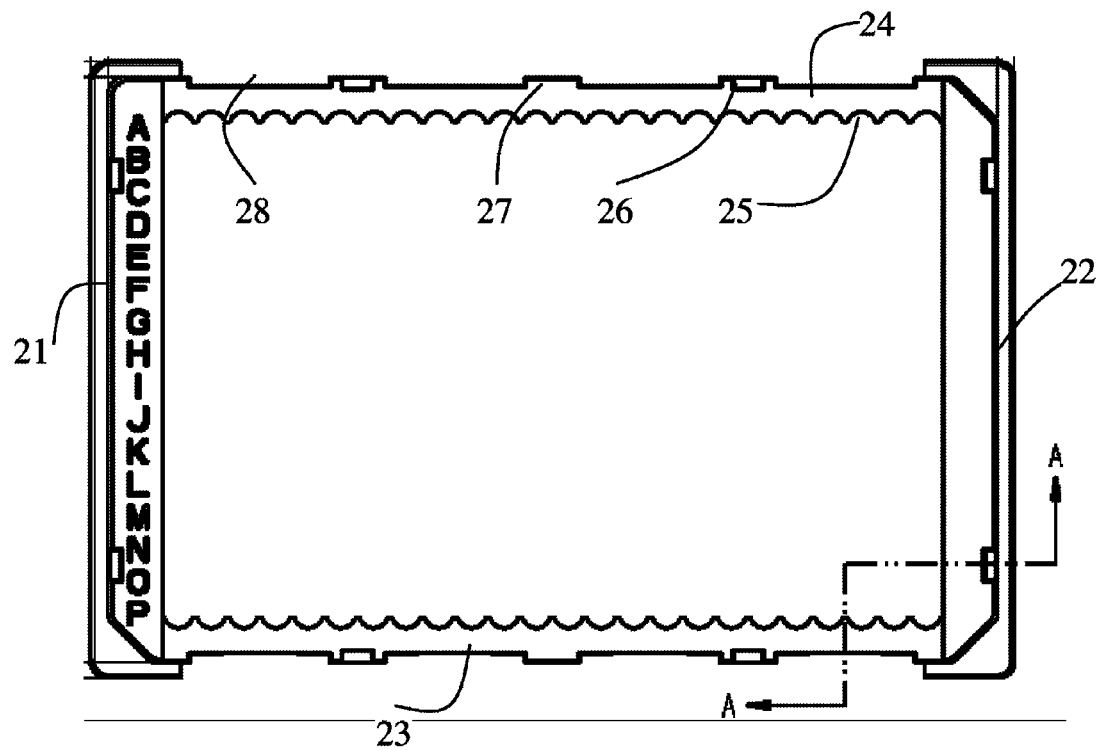
FIG. 2a illustrates a detailed top view of a tray according to an embodiment the invention.
Figure 2B:
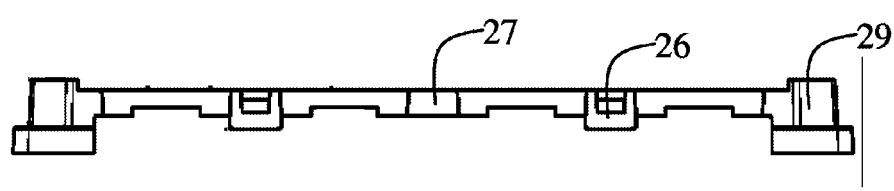
Figure 2C:
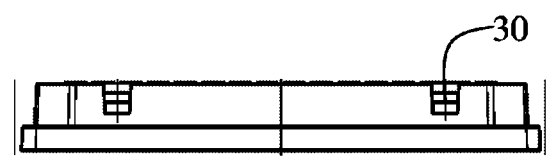
Figure 2D:
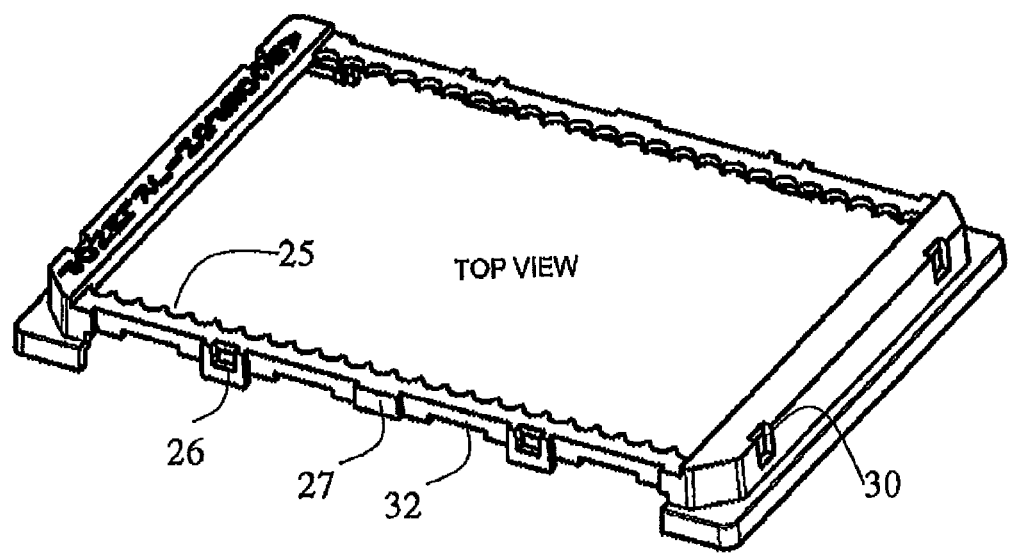
FIG. 2d shows a detailed perspective view of the tray of FIG. 2a seen from above.
Figure 2E:
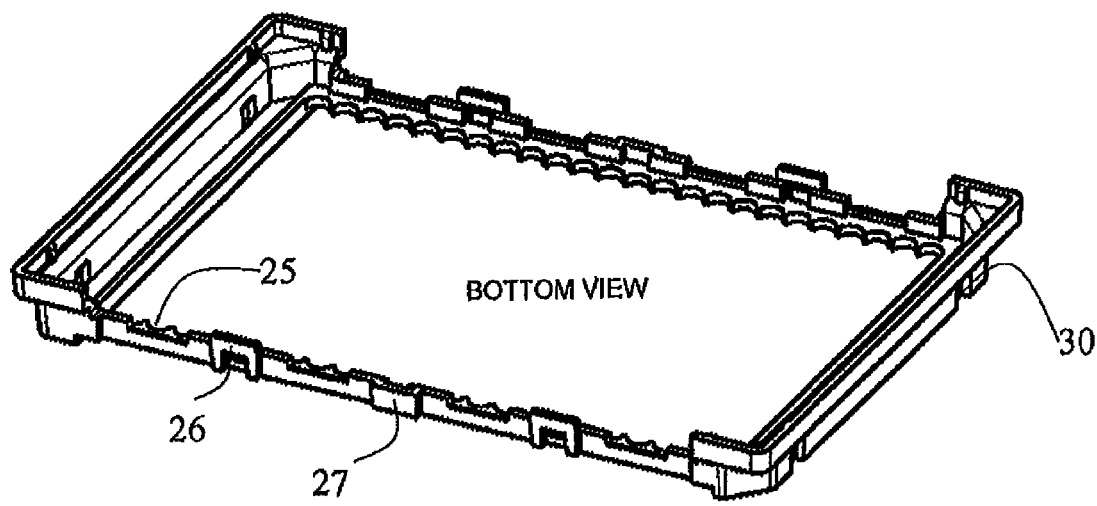
FIG. 2e shows a detailed perspective view of the tray of FIG. 2a seen from below.
Figure 3:
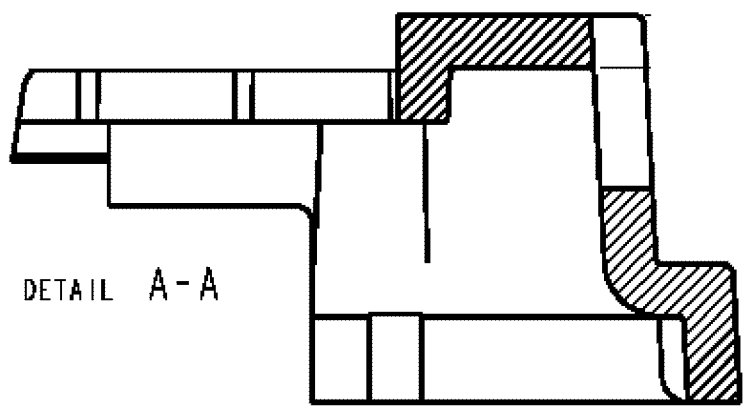

FIGS. 1a and 1b show the kit according to one embodiment of the invention. FIG. 1a shows a preferred assembling mechanism of the system. The tray is denoted with the reference numeral 10 and the four sample plates with the numerals 11-14. FIG. 1b shows the kit in an assembled condition, whereby it resembles a conventional microtiter plate.

FIGS. 2a to 2e show a preferred embodiment of the tray assembly for 4×96 (=384) wells. The tray comprises a set of two generally elongated parallel members 21 and 22 (in the following also denoted "first members"), and a set of two generally elongated parallel members 23 and 24 (i.e. "second members"). The first members are coupled to the ends of the second members from their ends such that a rectangular frame is formed. The frame defines a central opening. The second members may have a wave-shaped inner edge 25 in order to closely fit to the outermost well column of a plate. Alternatively, the inner edge can be generally straight, for example, in the case of a multipurpose tray, which can be used with plates of various sizes.

Mounting means, such as guiding members 26 and 27, are preferably provided on the inner or outer edge of the second members. The guiding members prevent possible movements of the sample plates in the horizontal direction (along the members) and assist in placing the plates into the tray such that the wells protrude into the central opening. Furthermore, slots 32 (or equivalent) can be provided for enabling releasable locking of the plates to the tray.

Figure 4A:
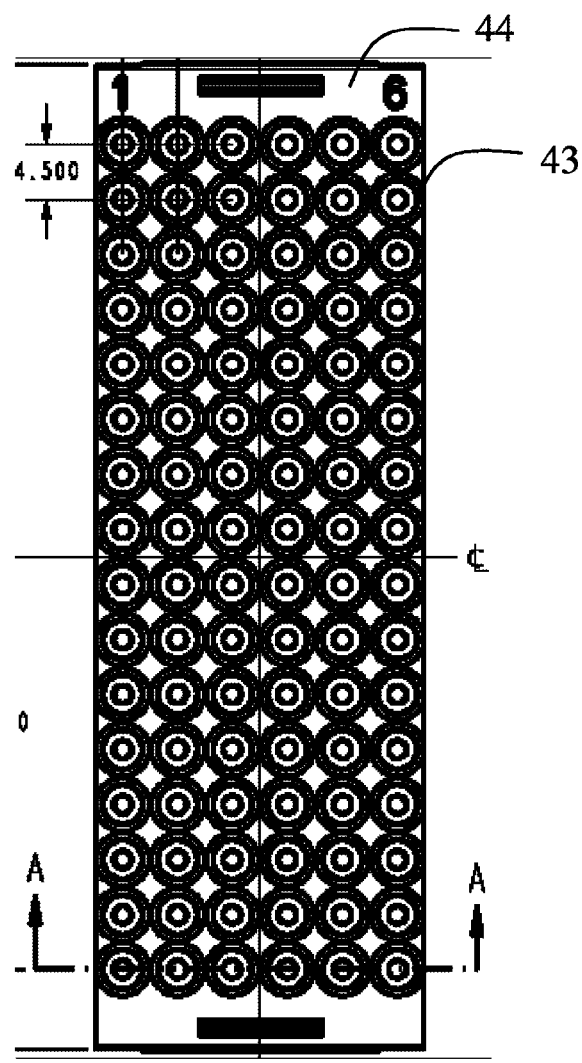
FIG. 4a shows a top view of a slide-sized plate according to an embodiment of the invention.
Figure 4B:
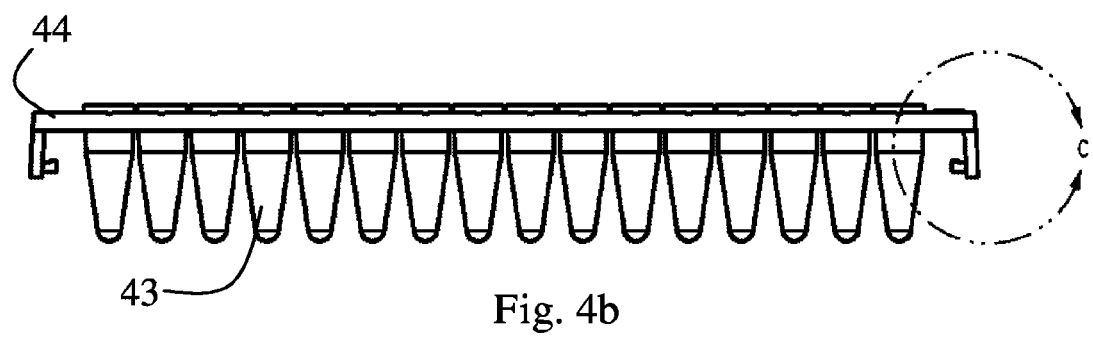
Figure 4C:
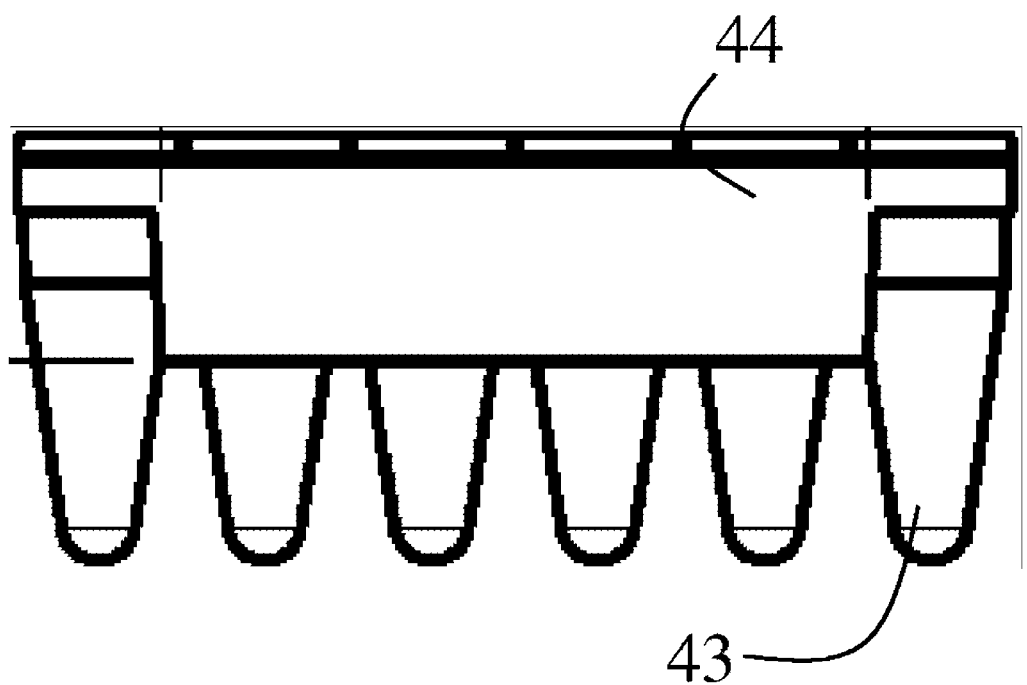
Figure 5A:
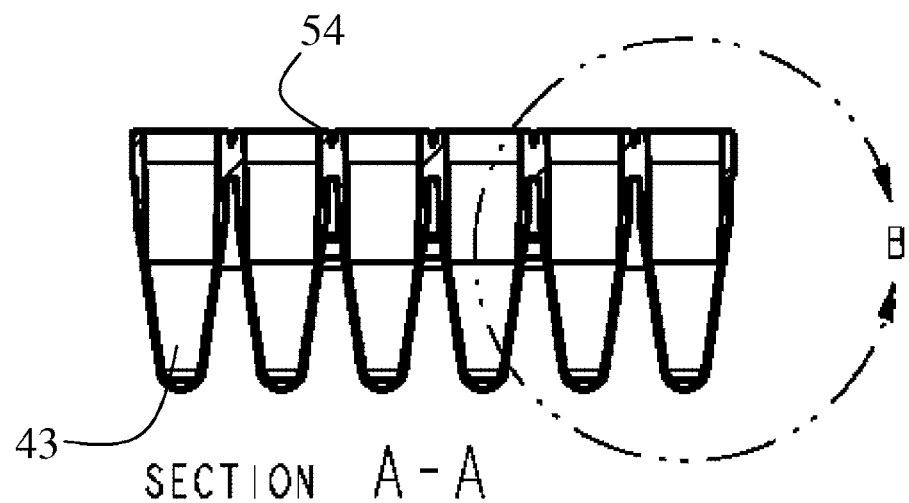
Figure 5B:
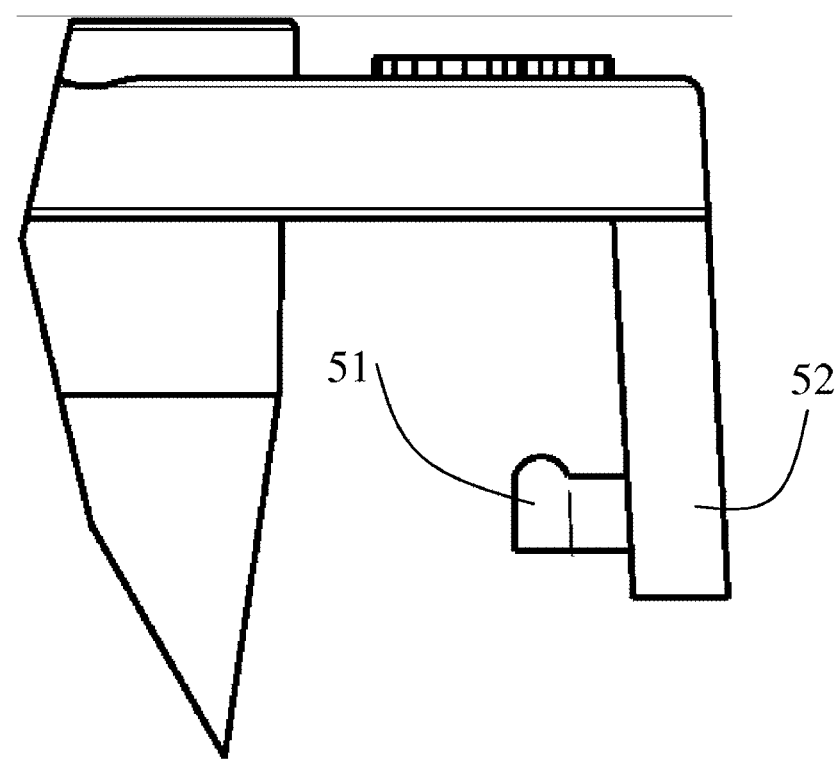
FIG. 5b shows a cross-sectional view of the plate detail C shown in FIG. 4b.

FIGS. 4a-4c show one embodiment of the sample plate. In FIG. 4a, the vertical dimension of the plate corresponds to the first dimension and the reduced horizontal dimension to the second dimension of a standard plate (i.e. an SBS plate). The wells 43 are arranged in a grid having a given well center-to-well center pitch. On two ends of the plate, there are plate mounting means, such as extensions 44, which are designed to fit into a tray. On the extensions 44, there may be slots which can be used by plate-handling robots in order to mount and remove the plates from the tray. Referring to FIG. 5b, which depicts a detail C shown in FIG. 4b, the extension 44 may comprise a horizontal part 53, a vertical part 52, and a tip 51, which locks the plate into the tray by slipping into a slot 32.

The format of the 96-well slide-sized plate is 6×16 samples with a center-to-center pitch for adjacent wells of 4.5 mm. That is, four of these plates can be mounted their long sides next to each other in an appropriate tray to form a SBS standard-sized 384-well microtiter plate. The maximum sample volume will be 50 µl. The plate can be sealed by any of the following methods which will allow for efficient sealing to as low as 2 µl reaction volume with the application of pressure from the top:
1. heat-sealing films,
2. pressure sealing films,
3. cap strips, and
4. reusable sealing mats.

The wells of this plate are conical in nature, and allow for efficient transfer of heat from heating block to liquid in said wells, up to 50 µl, and removal of reaction volumes with standard pipeting tools. The material of the plates will be of polypropylene, or like material, that offers good thermal conductivity, hydrophobicity and low interference with molecular biological reactions.

The 384-well slide-sized plate will have a format of 12×32 samples, with a center-to-center pitch for adjacent wells of 2.25 mm. Four of these plates can be placed side by side in a tray to form a standard 1536-well plate. The maximum sample volume will be 20 µl. The plate will be sealed by any of the following methods which will allow for efficient sealing to as low as 1 µl reaction volume with the application of pressure from the top:
1. heat-sealing films,
2. pressure sealing films, and
3. reusable sealing mats.

Like in the 96-well version the wells are designed to allow for efficient heat transfer of samples, up to 20 µl volumes, and removal of low reaction volumes with standard pipeting tools.

Typically the number of plates mountable in a single frame is 2, 3, 4, 5, 6 or 8, but also such solutions are within the scope of the invention, where the number of plates and the number of well columns in the second dimension of the frame are equal, that is, each plate consists of a strip (1×N grid, where N is an integer 1 to 32) of adjacent wells.

The plates are preferably formed from a thermoplastic material, which will withstand the conditions typical for thermal processing of biological samples, involving heating cycles increasing the temperature up to more than 80° C. In addition, the material should exhibit good hydrophobicity and low interference with molecular biological reactions. Examples of suitable materials include various polyolefine grades, polyesters and polycarbonates. A particularly preferred material is polypropylene, preferably of a grade suitable for melt processing, e.g. by injection molding, pressure forming, vacuum forming, extrusion molding or blow molding. The polypropylene can be nucleated or non-nucleated and it can contain heat and light stabilizers, antistatic agents, antioxidant as well as fillers, such as mica, calcium carbonate, talc and wollastonite, and pigments, such as carbonate, titanium dioxide, carbon black, quinacridone, phtalocyanine blue and isoindolinone. Other thermoplastic resins suitable for the present purposes are various high-quality polyethylene, polybutylene and poly(ethyelene terephthalate) grades.

The sample plates are preferably made of polypropylene or some other PCR-compatible material known per se. The plate is typically non-coated but can also have a top coating comprising, for example, $SiO_2$, polyaniline or antibodies, depending on the application.

Either 96-well slide-sized plates, or four 384-well slide-sized plates will be capable of mating with a rigid frame so that the complete assembly resembles closely a standard microtiter-sized plate. The overall format of the mated frame/plate assemblies will be 16×24 wells for the 96-well slide-sized plates, and 32×48 wells for the 384-well slide-sized plates. Pertaining to the outer dimensions and properties, the frame itself will conform to SBS standards, and will be made of a material that is both rigid and heat-resistant, so that it holds the slide-sized plates in a regular and repeatable position, even after stresses caused by standard laboratory processes and conditions. The thermal conductivity from the individual plates to the tray assembly is also reduced because of the discontinuities in the material between the plates and the tray, which provides increased temperature ramping speeds. If desired, the materials of the plates and the tray can be different. Typically, the trays are manufactured from one of the materials listed above for the plates.

The addition or removal of a plate, or series of plates from the frame assembly can be accomplished manually, without the aid of tools, or alternatively can be incorporated into a robotic system, which will perform such tasks in an automated fashion.

As discussed earlier, the above embodiment comprising an open frame with a central opening for the plates and the wells therein, and further comprising fastening means for the plates at the edges of the frame members, is but one implementation of the general idea of the invention. It is also possible to replace the open frame structure with a similar tray having a central recess with a perforated backing plate. Alternatively, a planar structure with a central "plate receiving portion" is equally possible. In both of these alternative embodiments, the wells of the sample plate should be capable of placement into unrestricted heat transfer connection with the holder/heating means of the analyzing equipment. Therefore the backing or receiving plates need to be perforated to provide apertures for the wells or the bottom of the wells.

The mated frame/plate assembly will be compatible with general laboratory equipment and analytical instrumentation. Such general lab equipment includes centrifuges adapted to spin individual and stacked microtiter plates; thermal cyclers that accommodate v-bottom microtiter plates; simple heaters and chillers that accept microtiter plates; and liquid handlers that are designed to manipulate reactions in wells configured within a microtiter plate format. Examples of analytical instrumentation that will accept microtiter-sized plates are DNA automated sequencing systems, florescence and colorimetric plate readers, and real-time, quantitative PCR instruments.

In a typical application, the sample plates or the tray kit is used for performing a PCR process in a thermal cycler. Such cyclers comprise a sample holder, which is designed to receive the microtiter plate and to provide a thermal pathway between a heating/cooling element of the device and the sample wells. The heating/cooling element typically comprises a peltier module coupled to a power source and to a heat sink.

The sample holder is preferably made of metal. It can be machined out of a solid block of aluminum or silver. In general, the sample holder preferably has a low mass, such that the heat reservoir formed by it remains small and higher temperature ramping speeds can be achieved. General requirements for the block are good thermal conductivity and low heat capacity.

Although peltier modules provide a convenient way of heating and cooling the samples, also other method of heat transfer can be used. These include, for example, hot/cool air convection by using fans, liquid heater/coolant-based systems and mechanical contacting of the block with hot/cool reservoirs.

Typically in practice, power and control means in the form of electronic elements are provided for performing the essential functions of the PCR process. Software elements can be used to provide automated monitoring and a user interface element to the process. In addition, mechanical elements are provided to ensure that the tubes are seated tightly into the block, to assist in easy access to the samples and to secure and hold in place and contain all the components of the equipment. All of these elements can be easily designed by one skilled in the art.

The invention claimed is:

1. A kit for processing biological samples comprising a tray assembly and a plurality of sample plates designed to fit into the tray assembly, wherein
   the tray assembly comprises a generally rectangular frame having perpendicularly connected frame elements defining a central plate-receiving portion having a width and a length, whereby said tray assembly is capable of accommodating the sample plates side by side in the plate-receiving portion; and
   each of the sample plates contains a plurality of individual sample wells arranged in a grid, the dimension of the plate in a first direction being at maximum the width of the frame and the dimension of the plate in a second direction being at maximum half of the length of the plate-receiving portion of the frame,
   wherein the sample plates are microtiter plates suitable for thermal cycling according to the PCR process, thus being of a v-bottom-type, whereby the sample wells are adapted to at least partially protrude through the plate-receiving portion of the frame,
   wherein the frame elements of the tray assembly comprise slots,
   wherein the sample plates comprise extensions on opposing ends thereof, each of the extensions further comprising a horizontal part and a vertical part extending from the horizontal part, wherein each of the extensions extends beyond the exterior edge of the tray assembly horizontally and beyond the bottom edge of the tray assembly vertically, and
   further wherein each of the vertical parts comprises a tip which is adapted to lock the plate into the tray assembly by slipping the tip into one of the slots.

2. A kit according to claim 1, wherein the plate-receiving portion comprises a central opening or central recess.

3. A kit according to claim 2, wherein the opening or recess is defined by the frame elements.

4. A kit according to claim 1, wherein the plate-receiving portion comprises a perforated plate having apertures for the individual sample wells.

5. A kit according to claim 1, wherein the sample plates completely cover the plate-receiving portion of the tray assembly when placed adjacent in the tray along the length of the recess.

6. A kit according to claim 1, wherein there are four sample plates.

7. A kit according to claim 1, wherein the tray assembly and the sample plates comprise mounting means for assisting positioning and immobilizing of the sample plates in the frame.

8. A kit according to claim 7, wherein the frame elements have wave-shaped inner edges for tightly fitting against the walls of the wells of the sample plates on at least some part of the frame.

9. A sample plate for holding a plurality of biological samples, the plate comprising
   a plurality of wells arranged in a grid having a predetermined pitch;
   extensions on opposing ends of the plate, each of the extensions further comprising a horizontal part and a vertical part extending from the horizontal part; and
   a tip being arranged on each of said vertical parts, with the tip arranged on one of the vertical parts extending in a direction toward the tip arranged on the other vertical part of the plate, with each tip being adapted to lock the plate into a plate-receiving frame by slipping into a slot provided on the plate-receiving frame,
   wherein the sample plate is a v-bottom type microtiter plate suitable for thermal cycling according to the PCR process.

10. A sample plate according to claim 9, wherein the outer dimensions of the plate correspond to the outer dimensions of a slide-sized microarray for enabling simultaneous compatibility with microfluidics devices and microarray handling equipment.

11. A sample plate according to claim 10, wherein the plate is, approximately, 75 mm by 25 mm in size.

12. The kit according to claim 1, wherein the means for enabling addition of the plates to the frame in an automated fashion by a robotic system also enables removal of the plates from the frame.

13. The kit according to claim 12, wherein said means for enabling addition of the plates to and removal of the plates from the frame in an automated fashion by a robotic system comprise slots arranged on extensions provided on opposite ends of the sample plates.

* * * * *